United States Patent [19]

Waltke

[11] 4,056,585

[45] Nov. 1, 1977

[54] TOOTH DIE AND METHOD AND APPARATUS FOR MAKING THE SAME

[76] Inventor: Robert W. Waltke, 39-32 215th Place, Bayside, N.Y. 11361

[21] Appl. No.: 688,179

[22] Filed: May 20, 1976

[51] Int. Cl.² ............................................. A61C 13/08
[52] U.S. Cl. ......................................... 264/19; 32/11; 249/54; 425/175
[58] Field of Search .................. 425/127, 175; 249/54, 249/52, 61, 101, 96; 32/11, 40 R; 264/19, 17; 403/292, 296, 265, 266, 269

[56] References Cited

U.S. PATENT DOCUMENTS

| | | | |
|---|---|---|---|
| 3,153,283 | 10/1964 | Weissman | 32/40 R |
| 3,470,614 | 10/1969 | Kelly | 32/11 |
| 3,495,333 | 2/1970 | Kuhn | 425/175 X |

FOREIGN PATENT DOCUMENTS

| | | | |
|---|---|---|---|
| 1,008,489 | 5/1952 | France | 264/19 |
| 1,913,505 | 10/1970 | Germany | 264/19 |

Primary Examiner—J. Howard Flint, Jr.
Assistant Examiner—W. R. Briggs
Attorney, Agent, or Firm—Bauer, Amer & King

[57] ABSTRACT

An apparatus for and method of forming a unitary tooth die and stem that is cast as an integral part of a dental stone model and separable therefrom for use as a unitary article of manufacture.

15 Claims, 10 Drawing Figures

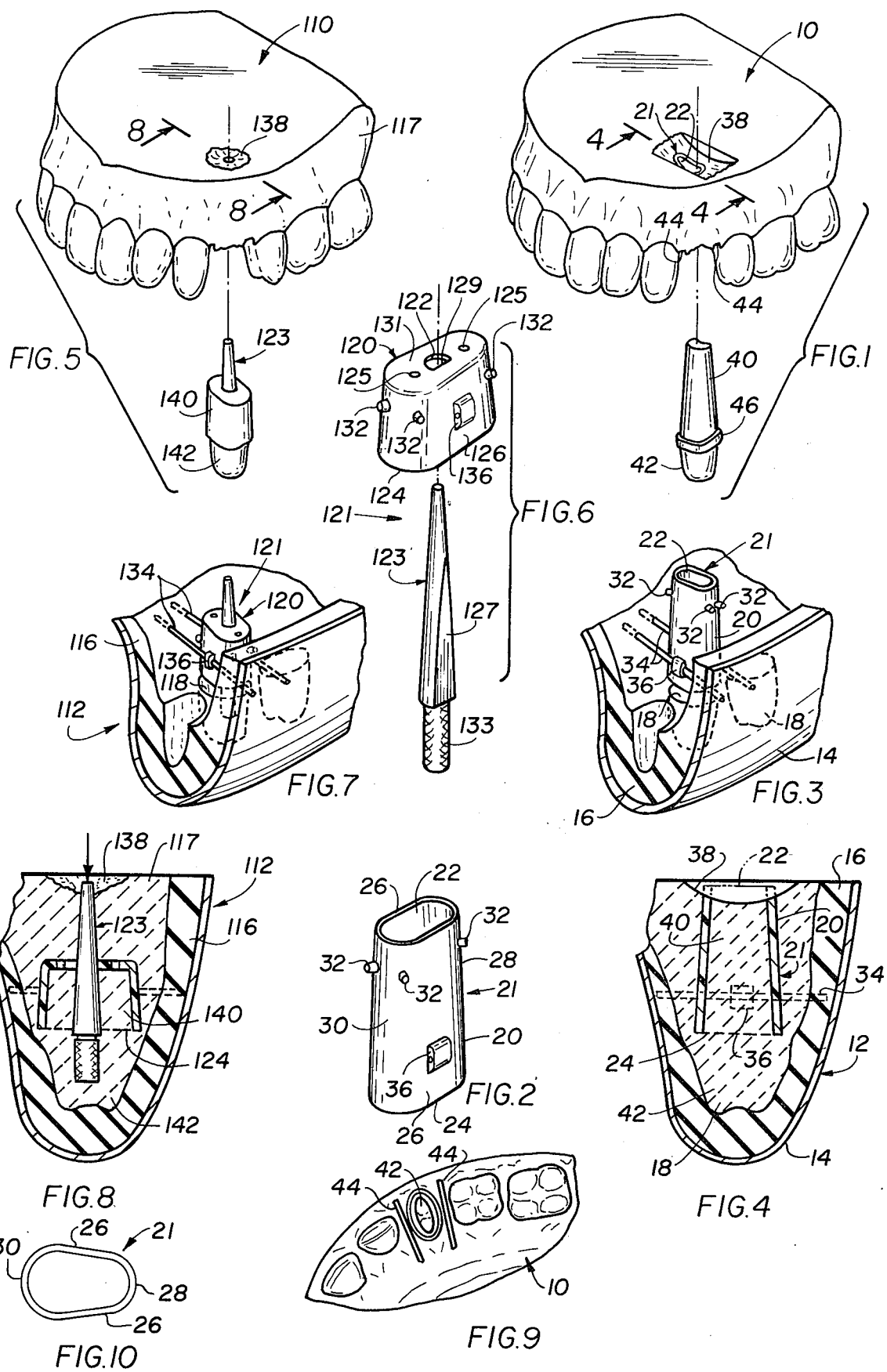

TOOTH DIE AND METHOD AND APPARATUS FOR MAKING THE SAME

This invention relates to making models of teeth and more particularly the invention relates to prosthetic dentistry whereby one or a plurality of individual teeth are separable from a dental casting or dental stone model.

In that aspect of dentistry which relates to tooth restoration, it is often required that an accurate dental model be made in a dental stone material of the affected tooth, or teeth. In making caps, crowns, bridges and the like, it is sometimes necessary to detach or separate from the dental model one or several individual tooth dies or models of selected teeth. In the performance of prosthetic procedures, the separable tooth die needs to be removed from, and repositioned back in, the model stone numerous times, and when so repositioned the tooth die must withstand considerable impact from hammering and grinding without the die shifting or changing its relationship to the remaining and adjacent teeth.

For example, in making a dental crown, the same is usually formed on one of the aforementioned separable tooth dies. During the working and shaping of the crown, the tooth die is sometimes placed back in the dental model stone where the crown is cold-worked into its final shape. Such cold-working places great strain on that portion of the tooth die that secures the die in the dental model stone. The cold-working also places equal but reactive strain on that portion of the model stone which is contiguous to and supports the tooth die stem or root. For an effective prosthetic system, the dental stone model and die need to withstand these forces of hammering and working.

In conventional devices, the tooth die stem or that part of the die that is received and seats in the dental stone model is generally of a slender or pin-like configuration. The transverse or lateral cross-section of this slender pin is considerably less than the transverse cross section of the crown part of the tooth die. Such construction severely strains the complementary stone portion in which the pin seats, and if this stone seat is not of proper design, the reactions of the pin on the stone seat or mold walls can permanently distort and damage or enlarge the stone seat. Such enlargement allows unwanted shifting of the tooth die when the die, or more particularly the crown prosthesis, is cold-worked. Because of the pin-like configuration of many conventional die stems, the self-alignment features often found on these conventional pins create problems owing to the stress concentrating nature of the pin. Hence, even if the pin has positioning flutes or fluted portions, the pin can still be, and often is, pushed or force-fit incorrectly in its stone seat of the dental model.

There are several prior constructions that neither singly nor in combination overcome the above-mentioned problems. For example, the U.S. Pat. to Kelly No. 3,470,614 teaches use of a relatively complicated and expensive pin and parting plate. A keying portion is employed to maintain alignment of the tooth die relative to the dental model stone when the former is placed back in the latter.

The U.S. Pat. to Weissman No. 3,153,283 employs a costly precision made fit of a pin and complementary sleeve.

Applicant's own U.S. Pat. to Waltke No. 3,453,736 taught a two-step pour process that required manual alignment of a tubular dowel.

Other U.S. Pat. Nos. of interest are: Cooper 3,286,350, Stern et al 3,454,256, Stern et al 3,469,316.

This invention relates to the use of an essentially simple hollow sleeve-like member for forming a self-sustaining stem that is cast and molded as a unitary part with its tooth die. The forming member is mounted within the negative impression of a denture containing the selected teeth to be treated. It is supported spaced from a selected tooth such that when the dental molding or casting material or stone is poured into the negative impression, the same flows into the forming member. When the dental material hardens, that portion of it contained in the forming member becomes the stem of the positive of the tooth relative to which the forming member was supported.

The resultant dental model contains the tooth die and stem as a unitary article formed integrally therewith but removable therefrom. This is simply accomplished because the forming member provides a fracture line along which the unitary stem and tooth die may be parted from the remaining dental model, while the forming member has a forming surface that is readily separable from the stem formed therein.

It is, therefore, an object of the present invention to provide a prosthetic apparatus for making tooth dies separable from a dental model stone.

It is another object of the present invention to provide a tooth die and complementary seat whereby the former can be placed back in the latter without misalignment of the tooth die with respect to adjacent teeth.

It is a further object of the present invention to provide a unitary stem and tooth die having a relatively enlarged transverse cross-section to provide a relatively large peripheral surface over which force is distributed.

It is a still further object of the present invention to provide an apparatus for making tooth dies that are separable from the remaining dental model stone wherein the apparatus is simple in design, easy to use and inexpensive to manufacture.

Other objects and features of the present invention will become apparent from the following detailed description when considered in connection with the accompanying drawing. It is to be understood, however, that the drawings are designed for purposes of illustration only and not as a definition of the limits of the invention for which reference should be made to the appending claims.

In the drawings wherein the same reference numeral denotes the same element throughout the several views:

FIG. 1 is a perspective view of a dental model and unitary tooth die and stem constructed according to the teaching of the invention;

FIG. 2 is a perspective view of a casting member of the type used in FIG. 1;

FIG. 3 is a perspective view of the casting member supported in a negative dental impression in accordance with the teaching of the invention;

FIG. 4 is a cross section of FIG. 1 taken along lines 4—4;

FIG. 5 is a perspective view of another dental model and another embodiment of a unitary tooth die and stem;

FIG. 6 is a perspective view of a casting member and die pin according to the teaching of the modified embodiment of FIG. 5;

FIG. 7 is a perspective view of the casting member and die pin of FIGS. 5 and 6 supported in a negative dental impression in accordance with the teaching of the invention;

FIG. 8 is a cross section of FIG. 5 taken along lines 8—8;

FIG. 9 is a plan view of either FIGS. 1 or 5 showing the unitary tooth die and stem molded integral with the dental model and before removal of the same therefrom; and FIG. 10 is a view of the open end of the casting member of either FIGS. 2 or 6.

Referring now to the drawing and more particularly to FIG. 1 thereof, the dental model there shown is generally identified by the numeral 10 in the form of a positive casting or molding formed of dental stone material. In the manufacture of the dental mode 10 which reproduces exactly as possible the denture that is to be worked upon, a negative mold is made of the denture.

In referring to FIG. 3, the negative mold or negative dental impression is generally identified by the numeral 12. It comprises a substantially rigid cup 14 into which an impression material 16 is contained. The cup with the material 16 is pressed against the denture to produce a negative impression and exact configuration conforming to that of the denture against which the same is impressed. In the construction shown in FIG. 3, the negative dental impression 12 contains the impression of a number of teeth 18 and the surrounding gum line.

Once the material 16 hardens, the negative dental impression 12 is then able to be utilized as an impression casting into which a dental molding material may be poured to produce a positive casting of the type illustrated in FIG. 1 and identified by the dental mold 10. The dental model 10 shown in FIG. 1 is in the position as it is removed from the negative dental impression 12.

To prepare for the casting of the dental model 10, a casting structure generally identified by the numeral 21 is utilized. The casting structure comprises a casting member 20 that is more clearly shown in FIG. 2. It comprises an elongated sleeve-like structure that may be tapered or narrowed along its length. It may be smaller at its one end 22 and larger at its other end 24. Each of the ends 22 and 24 is open in the embodiment of the casting member 20.

In referring to FIG. 10, it will be noted that although the casting member 20 is shown to have substantially planar sides 26 that narrow and merge with a curved wall 28 at one side and widen to merge with a curved wall 30 at the other side, this specific arrangement of details is not to be limiting upon the teaching of the invention. The interior shape or configuration of the casting member 20, as illustrated in the drawing and as described, should not constitute a limitation upon the scope of the present invention.

As the description proceeds, it will become apparent to the reader that the configuration shown is for illustrative purposes only. The intent is to show graphically that when an article, formed within the interior of the casting member 20, is removed therefrom, such article can be returned to the interior of the casting member 20 only in the same position that it assumed originally when it was cast and before it was removed. Hence, the casting member 20 and article formed therein must assume only one predetermined relationship and cannot assume any other non-predetermined relationship.

The interior of the casting member 20 is hollow throughout its length. The casting member 20 tapers from the wider end opening 24 toward the narrower end opening 22 to enable the accurate formation of a tooth die stem therein and for the rapid and easy removal of the formed tooth die stem therefrom. For this reason, therefore, the interior surface of the casting member 20 may be made of a material that easily separates and parts or releases from engagement with a molding material that is utilized to form the dental model 10 in a manner to be described.

It will be noted that for convenience, the casting member 20 is provided with protrusions or extensions 32 on the outer surface thereof. These protrusions or locking elements may be conveniently located on the casting member in any position or number to assure that when the casting member 20 is embedded in a molding material, the casting member will remain embedded in the material to become non-removable therefrom in a manner to be described.

The casting member 20 is adapted to be mounted over and in alignment with a selected or desired tooth cavity 18 formed in the negative dental impression 12. It is supported in its position spaced from the opening of the selected respective tooth 18 as shown in FIG. 3 by the use of supporting pins 34 which pass through eye type extensions or projections 36 defined along the planar side walls 26 of the casting member 20. The pins 34 are pressed into the soft impression material 16 of the negative dental impression 12 to support the casting member 20 as shown in FIG. 3. Those skilled in the art will recognize that there is a space between the opening of the tooth 18 and the open end 24 of the casting member 20. This space is maintained by the positioning of the supporting pins 34.

With the casting member 20 positioned over the desired tooth opening 18, a dental molding material 17, more commonly known as stone, is poured into the negative impression mold 12 to flow into the selected tooth impression or cavity 18 and then flows upward into the hollow interior of the casting member 20. A sufficient amount of dental mold material or stone 17 is poured into the negative dental impression 12 such as to insure that the whole outer surface of the casting member 20 is surrounded by the stone material so that the whole of the casting member 20 is covered by such stone material and becomes embedded therein to become and form an integral part thereof, as is illustrated in FIG. 4. When the dental stone material 17 hardens, a dental stone model 10 of the type illustrated in FIG. 1 is formed.

It will be noted that after the dental stone model 10 is formed, a relief or cavity 38 is cut away in the base of the dental model 10 to reveal and expose the narrow or smaller open end 22 of the casting member 20 to afford ready access thereto. Because the dental stone material 17 was permitted to flow into the hollow interior of the casting member 20, there is formed in the hollow of the member 20 a tooth die stem that is identified in FIG. 1 by the numeral 40. The tooth die stem 40 and the aligned tooth die 42 are unitary with each other with the tooth die 42 being a replica of the tooth cavity 18 in which the same was cast.

When access is provided to the smaller end 22 of the casting member 20 as illustrated in FIG. 1, access is also provided to the adjacent end of the tooth die stem 40. To remove the unitary tooth die and stem 42-40 from the dental stone model 10, a pair of saw cuts 44 are made in the dental model 10 bracketing the tooth die 42 as is shown in FIG. 9. These saw cuts are made in the stone model 10 to approximately the depth of the opening 24 at the other end of the casting member 20, thereby relieving much of the strength of the stone of the dental model 10 and reducing the stone connection between the tooth die 42 and the surrounding stone.

The release of the connection between the tooth die 42 and the surrounding stone of the model 10 now enables the unitary stem 40 and tooth die 42 to be removed from the stone model. This is accomplished simply by tapping or applying a force to the narrow end of the stem 40 at the opening 22 afforded by the cavity 38. Because the interior surface of the casting member 20 has a low co-efficient of adhesion and readily parts from the stone forming the stem 40, the force to be applied to the exposed narrow end of the stem 40 at the opening 22 in the cavity 38 is relatively small. It need be only of sufficient amount to overcome the connection between the remaining stone surrounding the tooth die 42. The rim defined by the opening 24 of the casting member 20 reduces the strength of connection between the tooth die 42 and the surrounding stone and provides an effective parting or cleavage line between the two. Illustrated in FIG. 1 is a peripheral rim 46 that results from the ready cleaved separation of the unitary tooth die stem 40 and die 42 from the remaining stone model with which the same was originally formed as an integral part thereof.

Because the stem 40 assumes whatever regular or irregular configuration that the casting member 20 was provided with at its interior surface, the same can only be returned to the stone model 10 and its seat within the casting member 22 in the same predetermined position that it was removed therefrom. The casting member 20 is solidly embedded and retained as an integral cast part of the dental model stone 10 and, thus, always forms a smooth conforming configured receptive holder for the unitary tooth die and stem 42-40. From what has been disclosed, it will be recognized that it is impossible to return the unitary tooth die and stem 42-40 to the dental model 10 in any manner other than in the predetermined manner in which the same was removed therefrom. Because of the relatively large size and length of the stem 40, the same readily supports and resists forces and stresses that may be applied to the same during the use of the tooth die 42 by a laboratory technician.

The embodiment illustrated in FIGS. 5 through 8 inclusive draws upon substantially the same teaching as that described with respect to the invention previously disclosed herein. In this regard, similar parts are identified by the same tens digits but are numbered in the 100 series. Thus, there is disclosed a dental model 110 which is a replica of a denture formed in the negative dental impression 112 as illustrated in FIGS. 7 and 8.

In FIGS. 7 and 8, the dental stone model 110 has embedded within it a casting structure generally identified by the numeral 121 and more clearly illustrated in FIG. 6. The casting structure 121 is much like the casting structure 21 previously described in the prior embodiment except that the same utilizes two parts rather than a single part. One of the parts is a tapered casting member generally identified by the numeral 120 and a tooth die dowel generally identified by the numeral 123. The casting member 120 is provided with an enlarged open end 124 and a relatively smaller opposite opening 122. Instead of being fully open at both of its ends as in the prior casting member 20, the present casting member 120 is provided with a plurality of small weep holes 125 which permit the weep or seepage of air trapped in the cup-like smaller end of the casting member 120 to be relieved therefrom.

As in the prior embodiment, the casting member 120 is provided with a plurality of molding projections 132 to assure that when the casting or molding dental stone is poured into the negative dental impression 112, the same will harden and adhere to the projections 132 to prevent the possible displacement of the casting member 120 from within the dental stone model 110 after the same is completed. The narrower or smaller opening 122 may be completely circular or it may be provided with an irregular configuration that is adapted to conform to and predeterminate position the dowel pin 123 that fits therewithin.

In the embodiment shown in FIG. 6, the dowel pin is provided with a flat surface 127 which mates with the flat surface 129 defining a part of the opening 122. The dowel pin is tapered so that its smallest and narrower end extends through and projects beyond the base 131 of the cup-like casting member 120. The opposite end of the pin 123 is provided with a knurled or otherwise roughened surface 133 to ensure that stone casting material will harden thereabout and not flake away therefrom.

The casting structure generally identified by the numeral 121 is positioned within the negative dental impression 112 in the same manner as described with respect to the prior embodiment. That is to say, the planar sides 126 are provided with eye-like extensions 136 through which supporting pins 134 are extended into engagement with the impression material 116 as illustrated in FIGS. 7 and 8. The casting member 120 is supported spaced in alignment above the selected tooth die cavity 118 in which a tooth die is to be reproduced with the roughened end 133 of the pin 123 extending into such cavity 118.

Thereafter, the dental molding material 117 is poured into the negative impression 112 so that the material flows into the cavity 118 and also upward into the hollow interior of the casting member 120 filling the same completely. Any entrapped air or moisture within the casting member 120 will be permitted to seep and weep outward and upward therefrom through the holes 125. When a sufficient amount of casting stone or material 117 is poured into the impression 112, the same is permitted to harden. As seen in FIG. 8, it will be noted that the casting material flows into the interior of the member 120 and fully about the dowel pin 123 so as to form a tooth die 142 having a unitarily formed stem 140, both of which are formed about a dowel pin 123.

The unitary tooth die and stem 142-140 are then removed from the model 110 by relieving the top of the model at 138 to provide access to the small end of the pin 123. Saw cuts are made bordering the tooth die 142 to approximately the depth of the open end 124 of the casting member, thereby relieving the connection between the tooth die and the surrounding stone. After this is done, a light tap on the exposed end of the dowel 123 causes the dowel and its surrounding stem 140 and unitary tooth die 142 to readily part from the surrounding stone and to be separated from the model 110 with which the same was integrally formed.

The structure of the embodiment illustrated in FIGS. 5 through 8 inclusive may be used in the same manner as that previously described. By reason of the large stone stem 140 formed unitary with the tooth die 142, the stem 140 provides a large surface of sufficient area that may be easily manipulated and which will readily support forces that are applied thereto during the use of the same by the laboratory technician. Because of the original configuration of the interior surface of the casting member 120, when it is necessary to return the unitary tooth die stem and die to the model 110, the same may only be returned in the same position that it was removed therefrom. Those skilled in the art will readily recognize that the retention of the casting member 120 within the stone model provides for an accurate re-seating and reception of the unitary tooth stem and die when it is necessary to return the same to the model.

While there have been shown and described and pointed out the fundamental novel features of the invention as applied to a preferred embodiment thereof, it will be understood that various omissions and substitutions and changes in the form and details of the device illustrated and in its operation may be made by those skilled in the art without departing from the spirit of the invention. It is the intention, therefore, to be limited only as indicated by the scope of the claims appended hereto.

I claim:

1. An apparatus including a negative dental impression mold for forming a tooth die and unitary stem as an integral part of a dental stone model and for separation from the dental stone model comprising
    a casting member having means supporting said member in a negative impression dental mold and to be spaced from the surfaces of said mold to enable molding stone poured into the dental mold to flow thereinto and about said member and means on the external surface of said member such that when the stone hardens to form the resulting dental stone model, said casting member is molded therein as an integral part thereof,
    positioning means cooperating with said casting member supporting means for supporting said member spaced in said mold,
    said casting member having an essentially hollow interior with a first opening at one end thereof for receiving the poured molding stone which flows into said hollow interior to form therein the stem of a tooth die having the length and cross-sectional shape of the defines of said hollow interior and that is unitary with a tooth die replica of a tooth impression of the negative dental impression mold,
    and said casting member having sidewalls tapering toward and first opening and a second opening opposite said first opening enabling the removal of the stone stem therefrom unitary with the tooth die.

2. An apparatus as in claim 1,
    an opening at the other end of said casting member, the hollow interior being smaller at one of its ends than at the other of its ends.

3. An apparatus as in claim 2,
    means on the exterior of said casting member to securely engage with the molding stone to retain said casting member as an integral non-separable part of the resulting dental stone model.

4. An apparatus as in claim 2,
    said casting member supporting means being on the exterior of said casting member and defining supports by which said casting member is supported in the negative impression dental mold and retained as an integral non-separable part of the resulting dental stone model.

5. An apparatus as in claim 2,
    the cross-sectional shape of said hollow interior of said casting member defining a configuration that prevents the return of the stone stem thereinto except in one predetermined position.

6. An apparatus as in claim 2,
    a die pin in said casting member extending through the hollow interior thereof and beyond said opening at said other end.

7. An apparatus including a negative dental impression mold for forming a dental model having a unitary tooth die and stem in which the tooth die is a replica of a tooth from the negative dental impression mold of a denture having a tooth comprising
    an essentially hollow stem forming member having an interior surface defining an open interior of predetermined configuration with an opening at one end thereof, said surface tapering toward said one end,
    means supporting said member in a position spaced apart from the negative dental impression mold of a tooth to be reproduced with said opening facing the tooth impression,
    said member having means on the external surface thereof to fix said member to dental material poured thereabout,
    said supporting means including means to engage with the negative dental impression mold and with said forming member such that when a dental material is poured into the negative dental impression mold, the material flows into the tooth impression and said open interior of said member through said opening to form a tooth die replica of a tooth that is unitary with a stem and which are integral with the remaining dental model.

8. An apparatus as in claim 7,
    said stem forming member having means for enabling the stem formed therein to be separated therefrom for the separation and removal of the unitary stem and tooth die from the dental model.

9. An apparatus as in claim 8,
    said opening defining a fracture line at which the unitary tooth die and stem separates from the dental model upon the removal of the same from the dental model.

10. An apparatus as in claim 9,
    the predetermined configuration of said open interior preventing the tooth die stem from being returned thereinto except in the relationship the same was removed therefrom.

11. An apparatus for forming by molding stone a unitary tooth die and stem therein with an integral dowel comprising
    a tooth stem forming member having an open interior of predetermined cross-section configuration for the reception of molding stone therein,
    a first opening at one end of said member to provide full access to said open interior for the flow of molding stone thereinto,
    said member having means on the external surface thereof to fix said member to dental material poured thereabout,
    opening means at the outer end of said member to provide limited access to said open interior,
    said member having sidewalls tapering toward said first opening,
    and a dowel pin having a smaller cross-section than said open interior in said forming member extending through said open interior through said first opening at said one end and through said member at said opening means at said other end.

12. An apparatus as in claim 11, and support means on said forming member to support the same in a dental impression mold.

13. An apparatus as in claim 11, the predetermined configuration of said open interior preventing the tooth die stem from being returned thereinto except in the relationship the same was removed therefrom.

14. An apparatus as in claim 11, said dowel pin having a stem of predetermined configuration such that the same is assembled in an opening in one predetermined relationship.

15. A method for forming a unitary tooth die and stem integral with and removable from a dental stone model comprising positioning a casting member having a hollow interior over and in alignment with and spaced from a negative impression of a denture having a cavity of a selected tooth to be reproduced, pouring a dental molding material into the negative impression and into the hollow of the casting member and cavity to form the stem of a tooth die that is integral with the tooth die reproduction formed by the material in the cavity of the selected tooth, allowing the molding material to harden into a dental stone model, relieving the dental stone model to provide access to a part of the die stem, and applying a force to the accessible part of the die stem to cleave and separate the unitary tooth die and stem from the casting member and dental stone model.

* * * * *

UNITED STATES PATENT OFFICE
CERTIFICATE OF CORRECTION

PATENT NO. : 4,056,585
DATED : November 1, 1977
INVENTOR(S) : ROBERT W. WALTKE

It is certified that error appears in the above-identified patent and that said Letters Patent are hereby corrected as shown below:

Column 7, line 49, after "toward" change "and" to --said--

Column 8, line 62, change "outer" to --other--

Column 9, line 16, change "for" to --of--

Signed and Sealed this

Seventh Day of February 1978

[SEAL]

Attest:

RUTH C. MASON
*Attesting Officer*

LUTRELLE F. PARKER
*Acting Commissioner of Patents and Trademarks*